(12) United States Patent
Pühler et al.

(10) Patent No.: US 9,381,177 B2
(45) Date of Patent: Jul. 5, 2016

(54) SUBSTITUTED N-(2-ARYLAMINO)ARYL SULFONAMIDE-CONTAINING COMBINATIONS

(75) Inventors: Florian Pühler, Berlin (DE); Marion Hitchcock, Berlin (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 421 days.

(21) Appl. No.: 13/877,204

(22) PCT Filed: Sep. 29, 2011

(86) PCT No.: PCT/EP2011/067041
§ 371 (c)(1),
(2), (4) Date: Jun. 6, 2013

(87) PCT Pub. No.: WO2012/041987
PCT Pub. Date: Apr. 5, 2012

(65) Prior Publication Data
US 2013/0261120 A1 Oct. 3, 2013

(30) Foreign Application Priority Data

Oct. 1, 2010 (EP) .................................... 10185800

(51) Int. Cl.
| | | |
|---|---|---|
| A61K 31/17 | (2006.01) |
| A61K 31/18 | (2006.01) |
| A61K 31/44 | (2006.01) |
| A61K 45/06 | (2006.01) |
| A61K 31/341 | (2006.01) |
| A61K 31/381 | (2006.01) |
| A61K 31/4035 | (2006.01) |
| A61K 31/415 | (2006.01) |
| A61K 31/42 | (2006.01) |
| A61K 31/426 | (2006.01) |
| A61K 31/433 | (2006.01) |
| A61K 31/496 | (2006.01) |
| A61K 31/5375 | (2006.01) |
| A61K 31/5377 | (2006.01) |
| C07C 275/40 | (2006.01) |
| C07C 311/08 | (2006.01) |
| C07D 209/46 | (2006.01) |
| C07D 209/48 | (2006.01) |
| C07D 213/75 | (2006.01) |
| C07D 213/81 | (2006.01) |
| C07D 231/18 | (2006.01) |

(Continued)

(52) U.S. Cl.
CPC .............. *A61K 31/18* (2013.01); *A61K 31/17* (2013.01); *A61K 31/341* (2013.01); *A61K 31/381* (2013.01); *A61K 31/4035* (2013.01); *A61K 31/415* (2013.01); *A61K 31/42* (2013.01); *A61K 31/426* (2013.01); *A61K 31/433* (2013.01); *A61K 31/44* (2013.01); *A61K 31/496* (2013.01); *A61K 31/5375* (2013.01); *A61K 31/5377* (2013.01); *A61K 45/06* (2013.01); *C07C 275/40* (2013.01); *C07C 311/08* (2013.01); *C07D 209/46* (2013.01); *C07D 209/48* (2013.01); *C07D 213/75* (2013.01); *C07D 213/81* (2013.01); *C07D 231/18* (2013.01); *C07D 261/10* (2013.01); *C07D 277/36* (2013.01); *C07D 295/135* (2013.01); *C07D 307/64* (2013.01); *C07D 333/34* (2013.01); *C07D 417/12* (2013.01)

(58) Field of Classification Search
CPC ........ A61K 31/17; A61K 31/18; A61K 31/44
See application file for complete search history.

(56) References Cited

U.S. PATENT DOCUMENTS

| 7,511,041 B2 | 3/2009 | Shimada et al. |
| 7,528,255 B2 | 5/2009 | Riedl et al. |

(Continued)

FOREIGN PATENT DOCUMENTS

| CN | 1341098 A | 3/2002 |
| CN | 1721397 A | 1/2006 |

(Continued)

OTHER PUBLICATIONS

Chinese Search Report issued in corresponding CN Patent Application 201180057294.6 (p. 1).

(Continued)

*Primary Examiner* — Samira Jean-Louis
(74) *Attorney, Agent, or Firm* — Miller, White, Zelano, Branigan, P.C.

(57) ABSTRACT

The present invention relates to:
combinations of:
component A: one or more omega-carboxyaryl-substituted diphenyl urea compounds of general formula (I), or a physiologically acceptable salt, solvate, hydrate or stereoisomer thereof;
component B: one or more N-(2-arylamino)aryl sulfonamide compounds of general formula (II), or a physiologically acceptable salt, solvate, hydrate or stereoisomer thereof; and, optionally,
component C: one or more further pharmaceutical agents;
in which optionally some or all of the components are in the form of a pharmaceutical formulation which is ready for use to be administered simultaneously, concurrently, separately or sequentially.
dependently of one another by the oral, intravenous, topical, local installations, intraperitoneal or nasal route;
use of such combinations for the preparation of a medicament for the treatment or prophylaxis of a cancer; and
a kit comprising such a combination.

10 Claims, 2 Drawing Sheets

Figure 1:
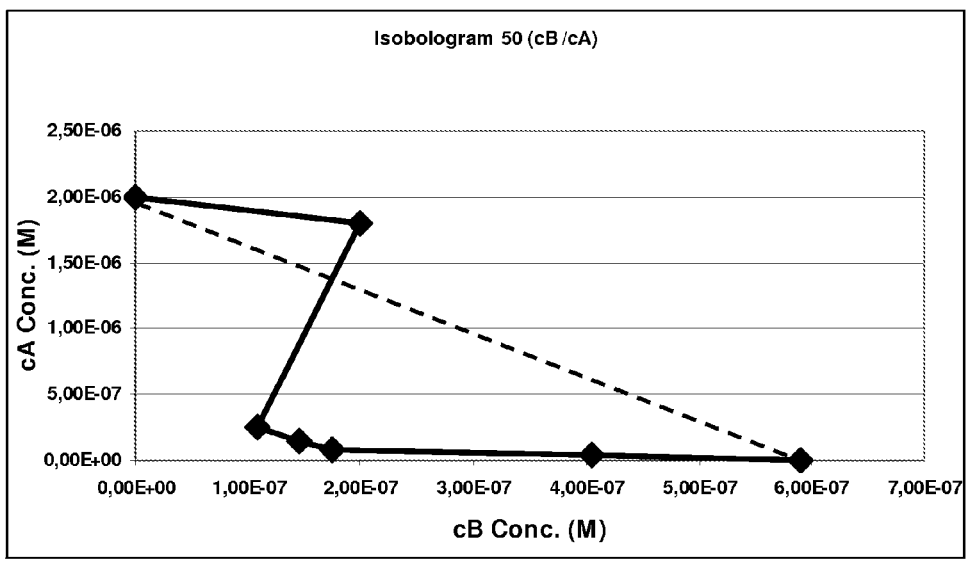

(51) Int. Cl.
  *C07D 261/10* (2006.01)
  *C07D 277/36* (2006.01)
  *C07D 295/135* (2006.01)
  *C07D 307/64* (2006.01)
  *C07D 333/34* (2006.01)
  *C07D 417/12* (2006.01)

(56) References Cited

U.S. PATENT DOCUMENTS

| | | | |
|---|---|---|---|
| 8,124,630 B2 | 2/2012 | Riedl et al. | |
| 8,124,782 B2 | 2/2012 | Logers et al. | |
| 8,129,386 B2 | 3/2012 | Shimada et al. | |
| 8,637,553 B2 | 1/2014 | Boyer et al. | |
| 2001/0011135 A1 | 8/2001 | Riedl et al. | |
| 2001/0011136 A1 | 8/2001 | Riedl et al. | |
| 2001/0016659 A1 | 8/2001 | Riedl et al. | |
| 2001/0027202 A1 | 10/2001 | Riedl et al. | |
| 2001/0034447 A1 | 10/2001 | Riedl et al. | |
| 2002/0042517 A1 | 4/2002 | Uday et al. | |
| 2003/0139605 A1 | 7/2003 | Riedl et al. | |
| 2003/0181442 A1 | 9/2003 | Riedl et al. | |
| 2003/0232765 A1 | 12/2003 | Carter et al. | |
| 2005/0038080 A1 | 2/2005 | Boyer et al. | |
| 2005/0059703 A1* | 3/2005 | Wilhelm | A61K 31/00 514/338 |
| 2006/0058358 A1 | 3/2006 | Dumas et al. | |
| 2006/0128732 A1 | 6/2006 | Shimada et al. | |
| 2006/0247186 A1 | 11/2006 | Carter et al. | |
| 2008/0032979 A1 | 2/2008 | Riedl et al. | |
| 2008/0058340 A1* | 3/2008 | Maderna | C07D 213/42 514/252.12 |
| 2008/0242707 A1 | 10/2008 | Schuckler et al. | |
| 2008/0262236 A1 | 10/2008 | Logers et al. | |
| 2009/0176791 A1 | 7/2009 | Sandner et al. | |
| 2009/0192127 A1 | 7/2009 | Scheuring et al. | |
| 2009/0215833 A1 | 8/2009 | Grunenberg et al. | |
| 2009/0270388 A1 | 10/2009 | Shimada et al. | |
| 2010/0035888 A1 | 2/2010 | Sandner et al. | |
| 2010/0173953 A1 | 7/2010 | Grunenberg et al. | |
| 2011/0060049 A1 | 3/2011 | Vernier et al. | |
| 2011/0098301 A1 | 4/2011 | Dixon et al. | |
| 2012/0015973 A1 | 1/2012 | Garraway et al. | |
| 2012/0040925 A1 | 2/2012 | Carter et al. | |
| 2012/0142742 A1 | 6/2012 | Riedl et al. | |
| 2013/0131122 A1 | 5/2013 | Boyer et al. | |

FOREIGN PATENT DOCUMENTS

| | | |
|---|---|---|
| CN | 1856469 A | 11/2006 |
| CN | 101495118 A | 7/2009 |
| WO | 00/42012 A1 | 7/2000 |
| WO | 03/047579 A1 | 6/2003 |
| WO | 2004/029055 A1 | 4/2004 |
| WO | 2005/009961 A2 | 2/2005 |
| WO | 2006/026500 A1 | 3/2006 |
| WO | 2006/034796 A1 | 4/2006 |
| WO | 2006/034797 A1 | 4/2006 |
| WO | 2006/094626 A1 | 9/2006 |
| WO | 2006/099231 A1 | 9/2006 |
| WO | 2007/014011 A2 | 2/2007 |
| WO | 2007/054215 A1 | 5/2007 |
| WO | 2007/054216 A1 | 5/2007 |
| WO | 2008/043446 A1 | 4/2008 |
| WO | 2008/120004 A1 | 10/2008 |
| WO | 2009/018238 A1 | 2/2009 |
| WO | 2010/068738 A1 | 6/2010 |

OTHER PUBLICATIONS

International Search Report for PCT/EP2011/067041 (Nov. 29, 2011).
C. Iverson et al., RDEA119/Bay 869766: A Potent, Selective, Allosteric Inhibitor of MEK1/2 for the Treatment of Cancer, Cancer Research, vol. 69, No. 17 (Sep. 1, 2009) pp. 6839-6847.
Written Opinion dated Apr. 21, 2015 issued in corresponding Singapore application 201302092-0 (pp. 1-11).
Chinese Search Report dated May 21, 2014 issued in corresponding Chinese Patent Application 201180057294.6 (pp. 1-8).
English Translation of Chinese Search Report dated May 21, 2014 issued in corresponding Chinese Patent Application 201180057294.6 (pp. 1-2).

* cited by examiner

Combination cB & cA in Hep3B cells
Isobologram IC50

|                  | cB_only  | 0.9cB+ 0.1cA | 0.7cB+ 0.3cA | 0.5cB+ 0.5cA | 0.3cB+ 0.7cA | 0.1cB+ 0.9cA | cA_only  |
|------------------|----------|--------------|--------------|--------------|--------------|--------------|----------|
| MAPPING IC50 (M) | 5,90E-07 | 4,50E-07     | 2.50E-07     | 2,90E-07     | 3,60E-07     | 2,00E-06     | 2.00E-06 |
| cB (M)           | 5,90E-07 | 4,05E-07     | 1.75E-07     | 1,45E-07     | 1,08E-07     | 2,00E-07     | 0        |
| cA (M)           | 0        | 4,50E-08     | 7.50E-08     | 1,45E-07     | 2,52E-07     | 1,80E-06     | 2.00E-06 |

Combination Index IC50

|      | 0.9cB+ 0.1cA | 0.7cB+ 0.3cA | 0.5cB+ 0.5cA | 0.3cB+ 0.7cA | 0.1cB+ 0.9cA |
|------|--------------|--------------|--------------|--------------|--------------|
| CI50 | 0,71         | 0,33         | 0.32         | 0,31         | 1,24         |

Isobologram IC50

| | cB_only | 0.9cB+ 0.1cA | 0.7cB+ 0.3cA | 0.5cB+ 0.5cA | 0.3cB+ 0.7cA | 0.1cB+ 0.9cA | cA_only |
|---|---|---|---|---|---|---|---|
| MAPPING IC50 (M) | 1,20E-05 | 8,50E-06 | 6,00E-06 | 4,10E-06 | 3,60E-06 | 3,20E-06 | 4,50E-06 |
| cB (M) | 1,20E-05 | 7,65E-06 | 4,20E-06 | 2,05E-06 | 1,08E-06 | 3,20E-07 | 0 |
| cA (M) | 0 | 8,50E-07 | 1,80E-06 | 2,05E-06 | 2,52E-06 | 2,88E-06 | 4,50E-06 |

Combination Index IC50

| | 0.9cB+ 0.1cA | 0.7cB+ 0.3cA | 0.5cB+ 0.5cA | 0.3cB+ 0.7cA | 0.1cB+ 0.9cA |
|---|---|---|---|---|---|
| CI50 | 0,83 | 0,75 | 0,63 | 0,65 | 0,67 |

SUBSTITUTED N-(2-ARYLAMINO)ARYL SULFONAMIDE-CONTAINING COMBINATIONS

The present invention relates:
to combinations of:
component A: one or more omega-carboxyaryl-substituted diphenyl urea compounds of general formula (I), or a physiologically acceptable salt, solvate, hydrate or stereoisomer thereof;
component B: one or more N-(2-arylamino)aryl sulfonamide compounds of general formula (II), or a physiologically acceptable salt, solvate, hydrate or stereoisomer thereof; and, optionally,
component C: one or more further pharmaceutical agents;
in which optionally either or both of components A and B in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

Another aspect of the present invention relates to the use of such combinations as described supra for the preparation of a medicament for the treatment or prophylaxis of a cancer, particularly hepatocyte carcinoma (which is also known as "hepatocellular carcinoma" and which is abbreviated to and additionally referred to hereinafter as "HCC"), lung cancer, in particular non-small cell lung carcinoma (abbreviated to and hereinafter referred to as "NSCLC"), colorectal cancer (abbreviated to and hereinafter referred to as "CRC"), melanoma, pancreatic cancer, or breast cancer.

Further, the present invention relates to:
a kit comprising:
a combination of:
component A: one or more omega-carboxyaryl-substituted diphenyl urea compounds of general formula (I), or a physiologically acceptable salt, solvate, hydrate or stereoisomer thereof;
component B: one or more N-(2-arylamino)aryl sulfonamide compounds of is general formula (II), or a physiologically acceptable salt, solvate, hydrate or stereoisomer thereof; and, optionally,
component C: one or more further pharmaceutical agents;
in which optionally either or both of said components A and B in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

BACKGROUND OF THE INVENTION

Combinations of RAF Inhibitors and MEK Inhibitors:

Omega-carboxyaryl diphenyl urea compounds, e.g. from published PCT applications WO 00/42012 A1, are known as inhibitors of the enzyme raf kinase. Since the enzyme is a down stream effector of $p21^{ras}$, the inhibitors are useful in pharmaceutical compositions for human or veterinary use where inhibition of the raf kinase pathway is indicated, e.g. in the treatment of tumours and/or cancerous cell growth mediated by raf kinase.

From published PCT application WO 2005/009961 A2 it is known that the omega-carboxyaryl diphenyl urea compound cited therein of formula (I) is a potent inhibitor of raf kinase, VEGFR kinase, p38 kinase and PDGFR kinase, which are all molecular targets of interest for the treatment and prevention of osteoporosis, inflammatory disorders, hyper-proliferative disorders, and angiogenesis disorders, including cancer.

Unexpectedly, and this represents a basis of the present invention, when combinations of:
component A: an omega-carboxyaryl-substituted diphenyl urea compound of general formula (I), or a physiologically acceptable salt, solvate, hydrate or stereoisomer thereof, as described and defined herein; with
component B: which is an N-(2-arylamino)aryl sulfonamide compound of general formula (II), or a physiologically acceptable salt, solvate, hydrate or stereoisomer thereof, as described and defined herein;
were evaluated for the treatment of hepatocyte carcinoma, synergistically increased anti-tumor activities were demonstrated with these combinations compared to each monotherapy, providing a fundamental rationale for the clinical combination therapy using:
a compound which inhibits a kinase as mentioned supra, in particular a raf kinase, and
a MEK inhibitor.

To the Applicant's knowledge, no generic or specific disclosure or suggestion in the prior art is known that either combinations of:
component A: one or more omega-carboxyaryl-substituted diphenyl urea compounds of general formula (I), or a physiologically acceptable salt, solvate, hydrate or stereoisomer thereof, as described and defined herein; with
component B: one or more N-(2-arylamino)aryl sulfonamide compounds of general formula (II), or a physiologically acceptable salt, solvate, hydrate or stereoisomer thereof, as described and defined herein; and, optionally,
component C: one or more further pharmaceutical agents, as described and defined herein;
in which optionally either or both of said components A and B of any of the above-mentioned combinations are in the form of a pharmaceutical formulation which is ready for use to be administered simultaneously, concurrently, separately or sequentially, would be effective in the treatment or prophylaxis of a cancer, particularly HCC, and may be effective in the treatment or prophylaxis of a cancer such as NSCLC, CRC, melanoma, pancreatic cancer or breast cancer.

Based on the action of the testing compounds described in this invention, the combinations of the present invention as described and defined herein, show a beneficial effect in the treatment of cancer, particularly HCC, and may be effective in the treatment or prophylaxis of a cancer such as NSCLC, CRC, melanoma, pancreatic cancer or breast cancer.

Accordingly, in accordance with a first aspect, the present invention relates: to combinations of:
component A: one or more omega-carboxyaryl-substituted diphenyl urea compounds of general formula (I), or a physiologically acceptable salt, solvate, hydrate or stereoisomer thereof, as described and defined herein; with
component B: one or more N-(2-arylamino)aryl sulfonamide compounds of general formula (II), or a physiologically acceptable salt, solvate, hydrate or stereoisomer thereof, as described and defined herein; and, optionally,
component C: one or more further pharmaceutical agents, as described and defined herein;
in which optionally either or both of said components A and B of any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with a second aspect, of the present invention relates to the use of any of such combinations as described supra for the preparation of a medicament for the treatment or prophylaxis of a cancer, particularly HCC, and may be effective in the treatment or prophylaxis of a cancer such as NSCLC, CRC, melanoma, pancreatic cancer or breast cancer.

Further, in accordance with a third aspect, the present invention relates to a kit comprising:
a combination of:
component A: one or more omega-carboxyaryl-substituted diphenyl urea compounds of general formula (I), or a physiologically acceptable salt, solvate, hydrate or stereoisomer thereof, as described and defined herein;
component B: one or more N-(2-arylamino)aryl sulfonamide compounds of general formula (II), or a physiologically acceptable salt, solvate, hydrate or stereoisomer thereof, as described and defined herein; and, optionally,
component C: one or more further pharmaceutical agents, as described and defined herein;
in which optionally either or both of components A and B in any of the above-mentioned combinations are in the form of a pharmaceutical formulation which is ready for use to be administered simultaneously, concurrently, separately or sequentially. The components may be administered independnently of one another by the oral, intravenous, topical, local installations, intraperitoneal or nasal route.

DETAILED DESCRIPTION OF THE INVENTION

In accordance with an embodiment of the above-mentioned aspects of the present invention, said combinations are of:
component A: which is one or more omega-carboxyaryl-substituted diphenyl urea compounds of general formula (I):

$$A\text{-}D\text{-}B \tag{I}$$

wherein
D is —NH—C(O)—NH—,
A is a substituted moiety of up to 40 carbon atoms of the formula: -L-$(M-L^1)_q$, where L is a 5 or 6 membered cyclic structure bound directly to D, $L^1$ comprises a substituted cyclic moiety having at least 5 members, M is a bridging group having at least one atom, q is an integer of from 1-3; and each cyclic structure of L and $L^1$ contains 0-4 members of the group consisting of nitrogen, oxygen and sulfur, and
B is a substituted or unsubstituted, up to tricyclic aryl or heteroaryl moiety of up to 30 carbon atoms with at least one 6-member cyclic structure bound directly to D containing 0-4 members of the group consisting of nitrogen, oxygen and sulfur,
wherein $L^1$ is substituted by at least one substituent selected from the group consisting of —$SO_2R_x$, —C(O) $R_x$ and —C($NR_y$) $R_z$,
$R_y$ is hydrogen or a carbon based moiety of up to 24 carbon atoms optionally containing heteroatoms selected from N, S and O and optionally halosubstituted, up to per halo,
$R_z$ is hydrogen or a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen;

$R_x$ is $R_z$, or $NR_aR_b$ where $R_a$ and $R_b$ are
a) independently hydrogen,
a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen, or
—$OSi(R_f)_3$ where $R_f$ is hydrogen or a carbon based moiety of up to 24 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen; or
b) $R_a$ and $R_b$ together form a 5-7 member heterocyclic structure of 1-3 heteroatoms selected from N, S and O, or a substituted 5-7 member heterocyclic structure of 1-3 heteroatoms selected from N, S and O substituted by halogen, hydroxy or carbon based substituents of up to 24 carbon atoms, which optionally contain heteroatoms selected from N, S and O and are optionally substituted by halogen; or
c) one of $R_a$ or $R_b$ is —C(O)—, a $C_1$-$C_5$ divalent alkylene group or a is substituted $C_1$-$C_5$ divalent alkylene group bound to the moiety L to form a cyclic structure with at least 5 members, wherein the substituents of the substituted $C_1$-$C_5$ divalent alkylene group are selected from the group consisting of halogen, hydroxy, and carbon based substituents of up to 24 carbon atoms, which optionally contain heteroatoms selected from N, S and O and are optionally substituted by halogen;
where B is substituted, L is substituted or $L^1$ is additionally substituted, the substituents are selected from the group consisting of halogen, up to per-halo, and Wn, where n is 0-3;
wherein each W is independently selected from the group consisting of —CN, —$CO_2R^7$, —C(O)$NR^7R^7$, —C(O)—$R^7$, —$NO_2$, —$OR^7$, —$SR^7$, —$NR^7R^7$, —$NR^7C(O)OR^7$, —$NR^7C(O)R^7$, -Q-Ar, and carbon based moieties of up to 24 carbon atoms, optionally containing heteroatoms selected from N, S and O and optionally substituted by one or more substituents independently selected from the group consisting of —CN, —$CO_2R^7$, —C(O)$R^7$, —C(O)$NR^7R^7$, —$OR^7$, —$SR^7$, —$NR^7R^7$, —$NO_2$, —$NR^7C(O)R^7$, —$NR^7C(O)OR^7$ and halogen up to per-halo; with each $R^7$ independently selected from H or a carbon based moiety of up to 24 carbon atoms, optionally containing heteroatoms selected from N, S and O and optionally substituted by halogen,
wherein Q is —O—, —S—, —N($R^7$)—, —$(CH_2)_m$—, —C(O)—, —CH(OH)—, —$(CH_2)_mO$—, —$(CH_2)_m$S—, —$(CH_2)_mN(R^7)$—, —$O(CH_2)_m$—$CHX^a$—, —$CX^a{}_2$—, —S—$(CH_2)_m$— and —$N(R^7)(CH_2)_m$—, where m=1-3, and $X^a$ is halogen; and
Ar is a 5- or 6-member aromatic structure containing 0-2 members selected from the group consisting of nitrogen, oxygen and sulfur, which is optionally substituted by halogen, up to per-halo, and optionally substituted by $Z_{n1}$, wherein n1 is 0 to 3 and each Z is independently selected from the group consisting of —CN, —$CO_2R^7$, —C(O)$R^7$, —C(O) $NR^7R^7$, —$NO_2$, —$OR^7$, —$SR^7$—$NR^7R^7$, —$NR^7C(O)OR^7$, —$NR^7C(O)R^7$, and a carbon based moiety of up to 24 carbon atoms, optionally containing heteroatoms selected from N, S and O and optionally substituted by one or more substituents selected from the group consisting of —CN, —CO$_2$R$^7$, —COR$^7$, —C(O)NR$^7$R$^7$, —OR$^7$, —SR$^7$, —NO$_2$, —NR$^7$R$^7$, —NR$^7$C(O)R$^7$, and —NR$^7$C(O)OR$^7$, with R$^7$ as defined above, with the proviso that said compound of general formula (I) is not:

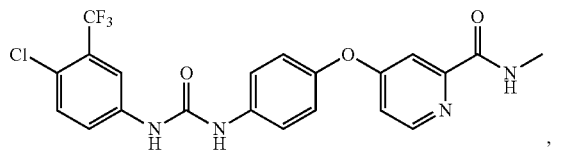

(which is compound Example entry 42 of WO 00/42012 A1: it is disclaimed from the definition of component A of the combinations of the present invention as described and defined herein);

or a physiologically acceptable salt, solvate, hydrate or stereoisomer thereof; said compounds are published as compounds of general formula (I) in International patent application PCT/US00/00648, published as WO 00/42012 A1 on Jul. 20, 2000, which is incorporated herein by reference in its entirety. In WO 00/42012 A1, said compounds of general formula (I) are described on pp. 2 et seq., they may be synthesized according to the methods given therein on pp. 14 et seq., and are exemplified as specific compound Example entries 1 to 41 and 43 to 103 on pp. 53 to 88, therein.

A further specific example of said compounds of general formula (I) of WO 00/42012 A1 is of structure (Ia), which is herein referred to as the "compound of formula (Ia)":

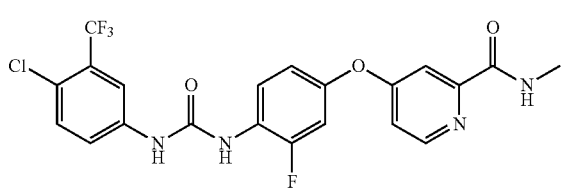

said compound of formula (Ia) is published as compound of formula (I) in International patent application PCT/US2004/023500, published as WO 2005/009961 A2 on Feb. 3, 2005, which is incorporated herein by reference in its entirety. Said compound of formula (Ia) is, in WO 2005/009961 A2, described on pp. 13 et seq. therein, it may be synthesized according to the methods given therein on pp. 45 et seq. therein, and is exemplified as specific compound Example 1 on p. 47 therein (free base), Example 2 on p. 47 therein (hydrochloride salt), Example 3 on p. 48 therein (mesylate salt), and Example 4 on p. 49 therein (phenylsulfonate salt).

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with another embodiment of the above-mentioned aspects of the present invention, said combinations are of: component A: which is one or more omega-carboxyaryl-substituted diphenyl urea compounds of general formula (I), supra, which is selected from the list consisting of:

specific compound Example entries 1 41 and 43 to 103 on pp. 53 to 88, of International patent application PCT/US00/00648, published as WO 00/42012 A1 on Jul. 20, 2000, which is incorporated herein by reference is in its entirety; or specific compound of formula (Ia), supra, which is published as the compound of formula (I) in International patent application PCT/US2004/023500, published as WO 2005/009961 A2 on Feb. 3, 2005, (which is incorporated herein by reference in its entirety), as specific compound Example 1 on p. 47 therein (free base), Example 2 on p. 47 therein (hydrochloride salt), Example 3 on p. 48 therein (mesylate salt), and Example 4 on p. 49 therein (phenylsulfonate salt);

or a physiologically acceptable salt, solvate, hydrate or stereoisomer thereof.

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

As mentioned supra, said specific compound Examples may be synthesized according to the methods given in WO 00/42012 A1, or WO 2005/009961 A2.

In accordance with another embodiment of the above-mentioned aspects of the present invention, said combinations are of:

component A: which is one or more omega-carboxyaryl-substituted diphenyl urea compounds of general formula (I), supra, which is selected from the list consisting of:

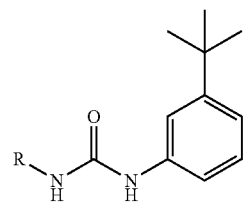

| Example entry | R |
|---|---|
| 1 | ![structure] |
| 2 | ![structure] |
| 3 | ![structure] |

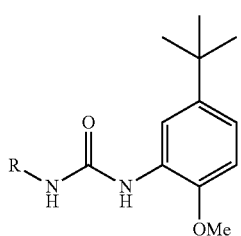
| Example entry | R |
|---|---|
| 4 | 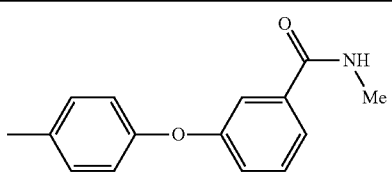 |
| 5 | 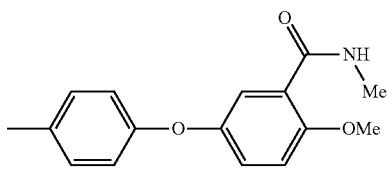 |
| 6 | 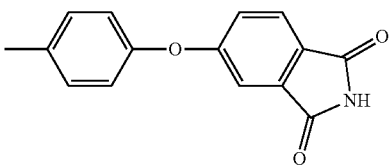 |
| 7 | 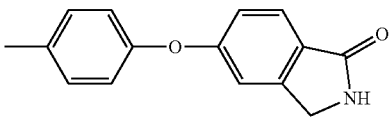 |
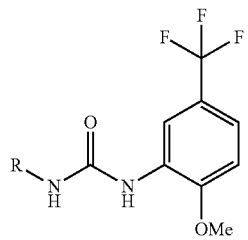
| Example entry | R |
|---|---|
| 8 | 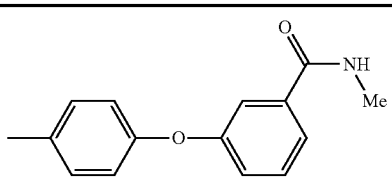 |
-continued
| Example entry | R |
|---|---|
| 9 | 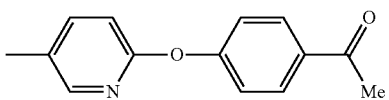 |
| 10 | 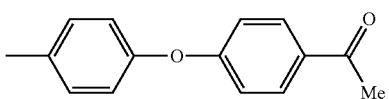 |
| 11 | 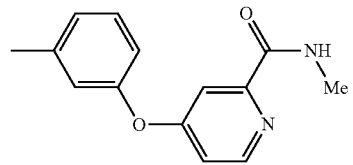 |
| 12 | 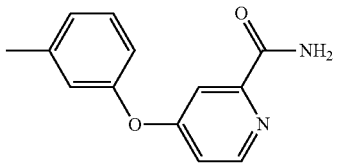 |
| 13 | 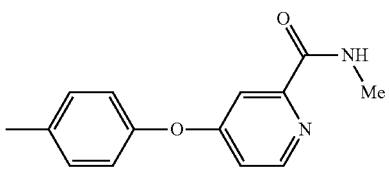 |
| 14 | 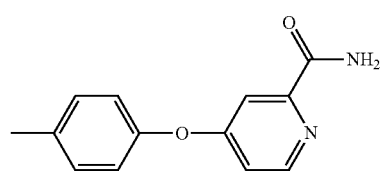 |
| 15 | 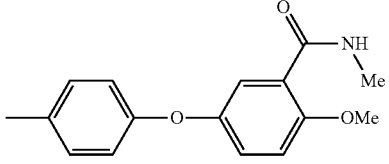 |
| 16 | 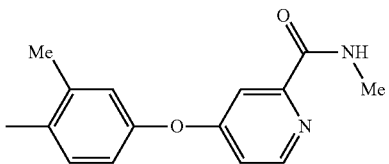 |
| 17 | 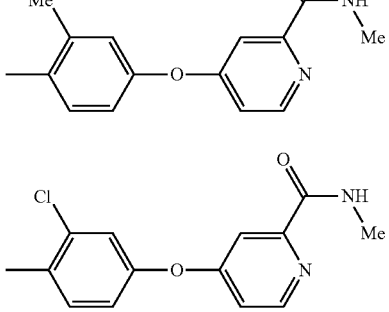 |

-continued
| Example entry | R |
|---|---|
| 18 | 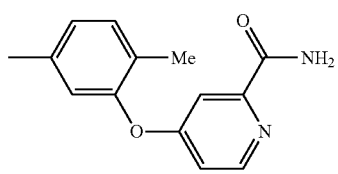 |
| 19 | 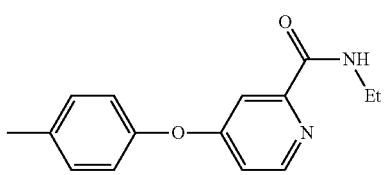 |
| 20 | 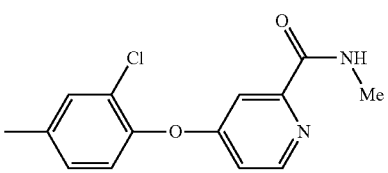 |
| 21 | 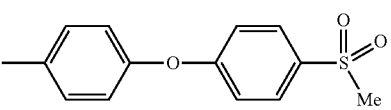 |
| 22 | 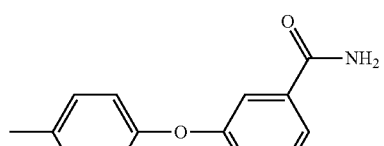 |
| 23 | 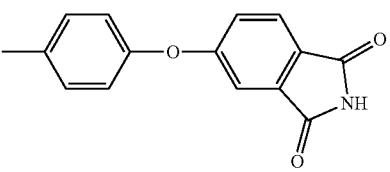 |
| 24 | 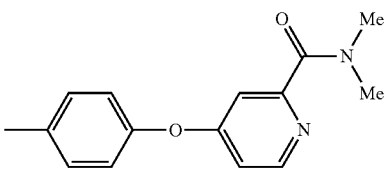 |
| 25 | 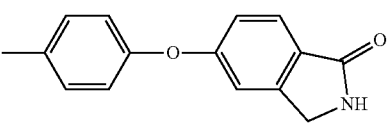 |
| 26 | 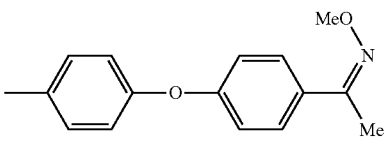 |
-continued
| Example entry | R |
|---|---|
| 27 | 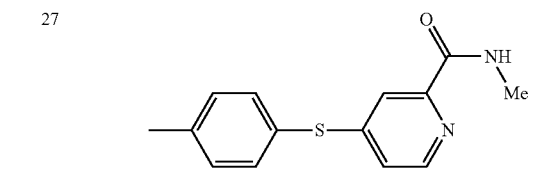 |
| 28 | 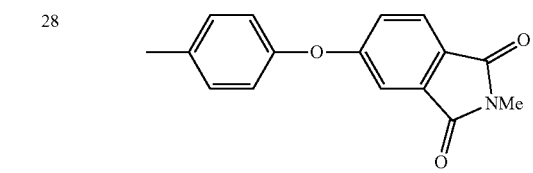 |
| 29 | 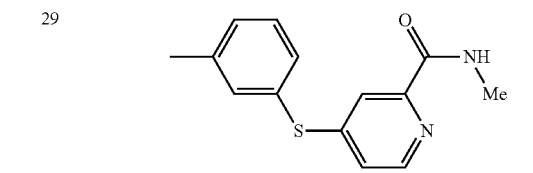 |
| 30 | 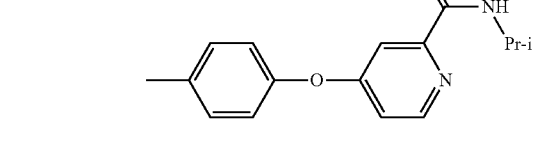 |
| 31 | 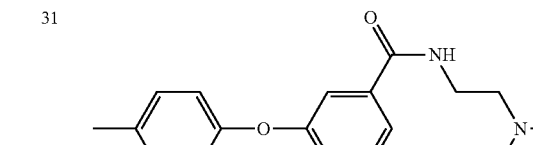 |
| 32 | 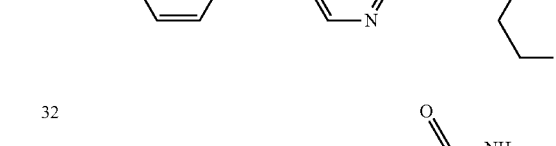 |
| 33 | 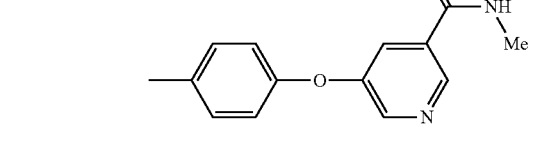 |
| 34 | 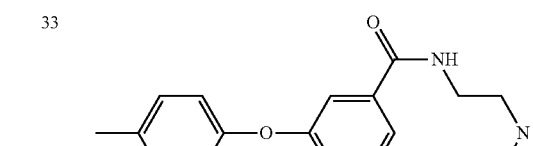 |

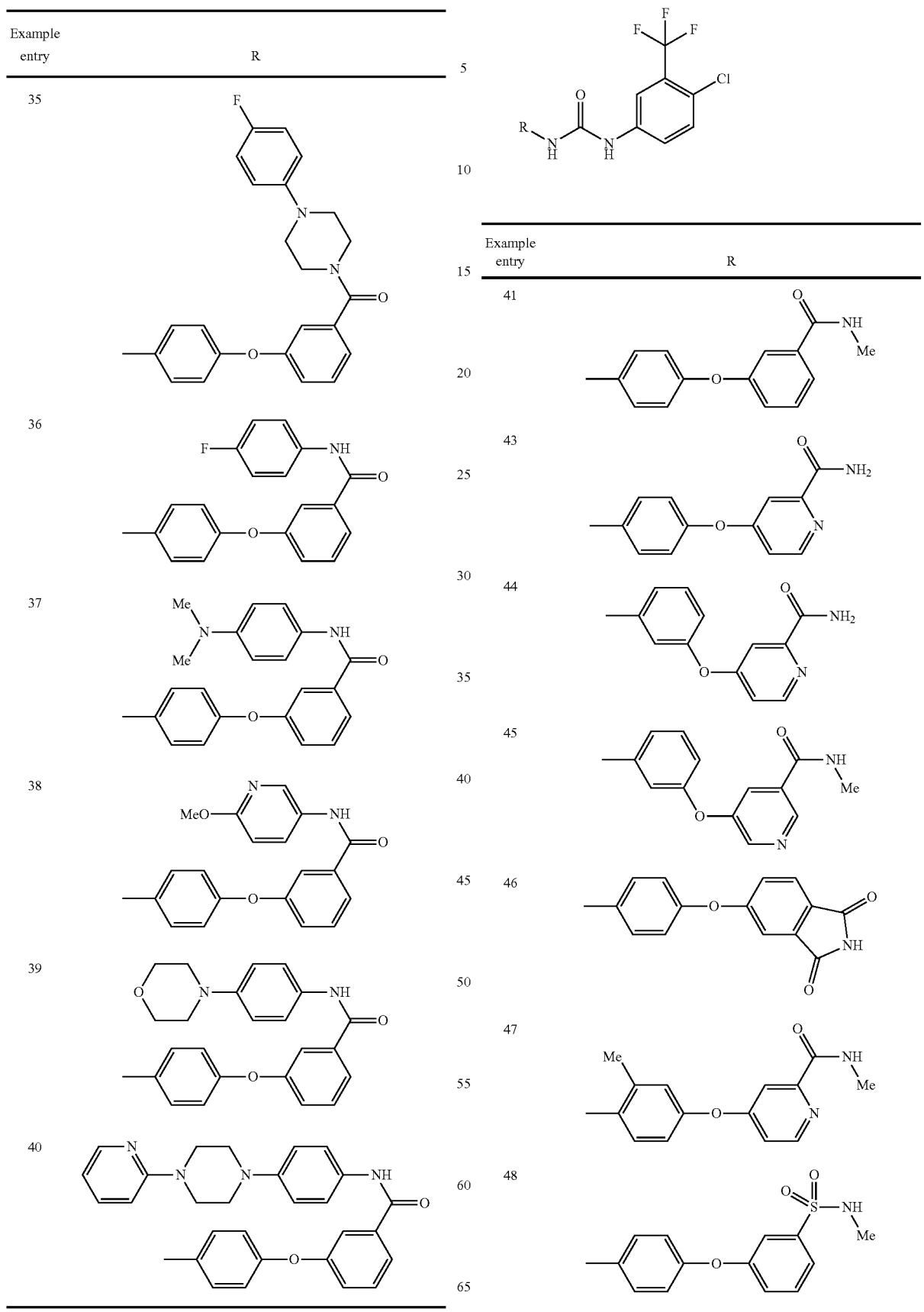

| Example entry | R |
|---|---|
| 49 | 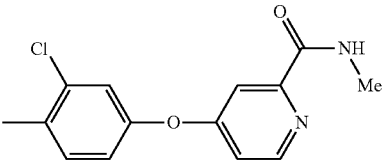 |
| 50 | 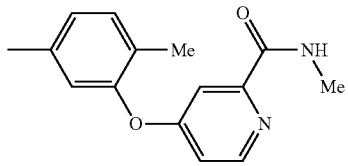 |
| 51 | 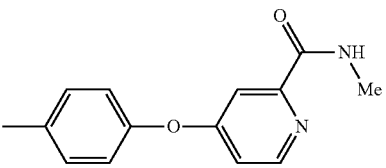 |
| 52 | 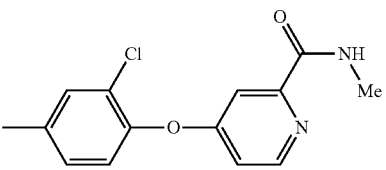 |
| 53 | 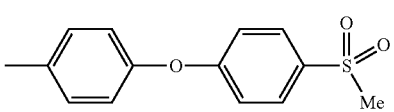 |
| 54 | 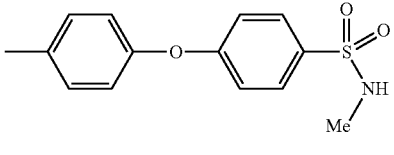 |
| 55 | 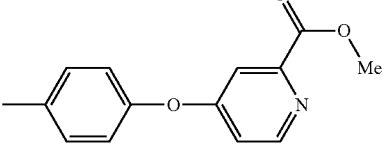 |
| 56 | 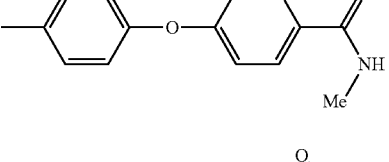 |
| 57 | 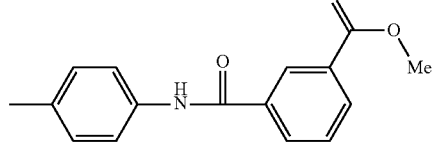 |
| 58 | 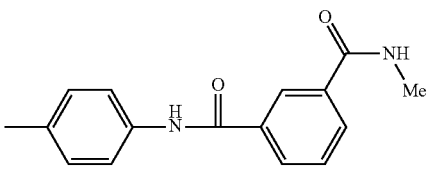 |
| 59 | 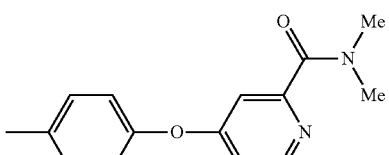 |
| 60 | 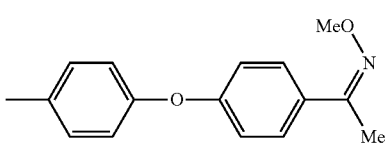 |
| 61 | 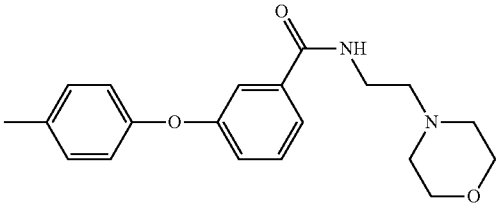 |
| 62 | 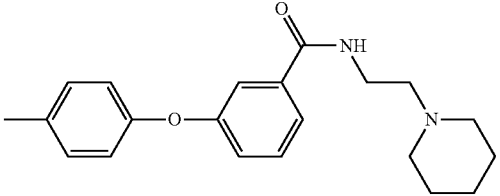 |
| 63 | 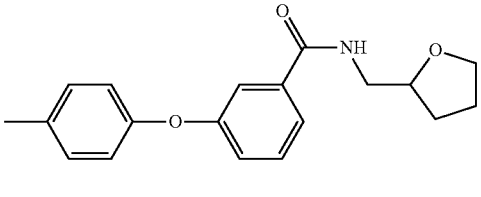 |
| 64 | 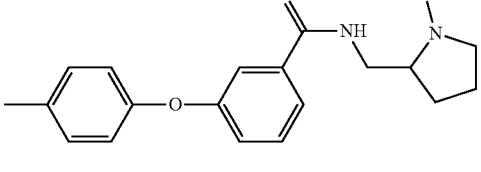 |
| 65 | 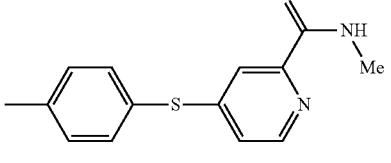 |

| Example entry | R |
|---|---|
| 66 | 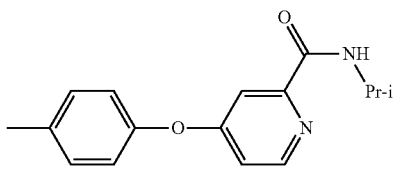 |
| 67 | 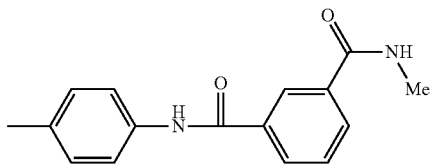 |
| 68 | 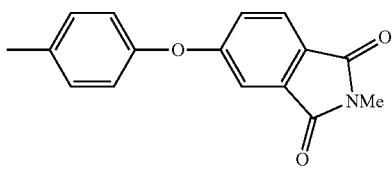 |
| 69 | 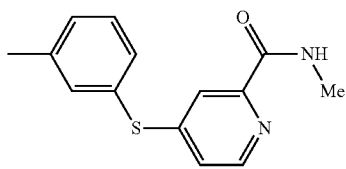 |
| 70 | 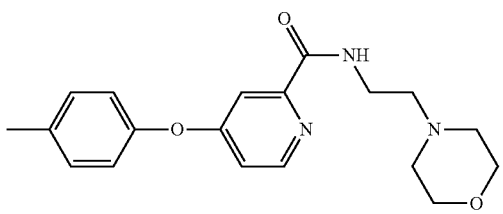 |
| 71 | 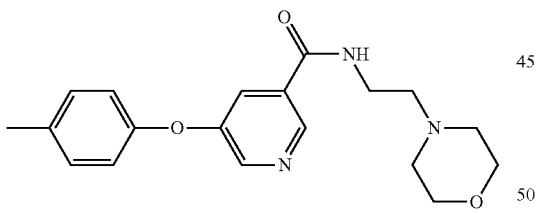 |
| 72 | 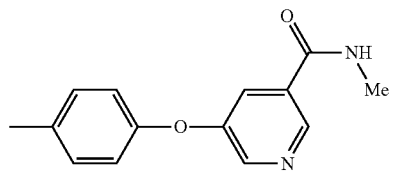 |
| 73 | 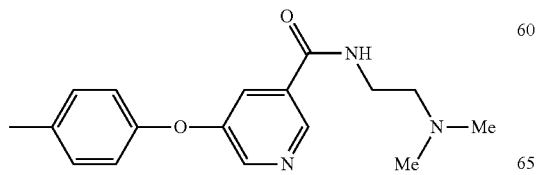 |
| 74 | 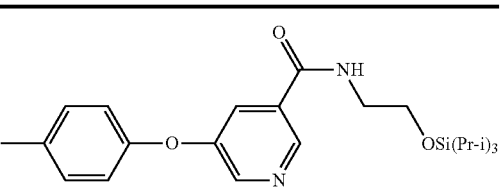 |
| 75 | 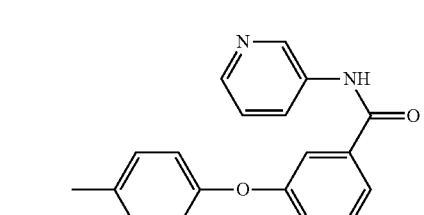 |
| 76 | 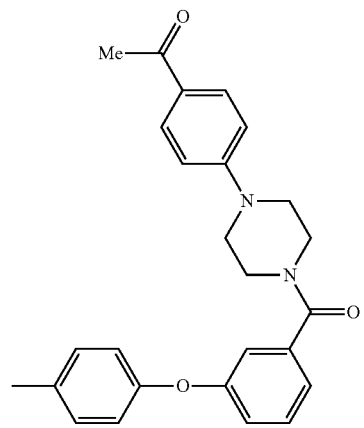 |
| 77 | 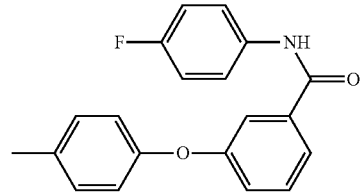 |
| 78 | 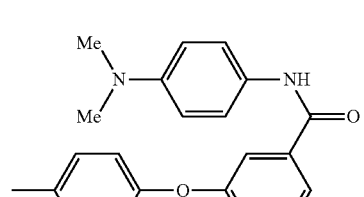 |
| 79 | 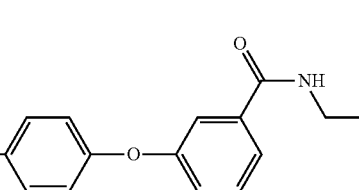 |

| Example entry | R |
|---|---|
| 80 | 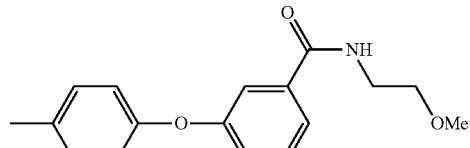 |
| 81 | 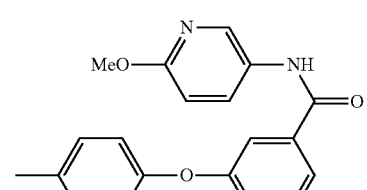 |
| 82 | 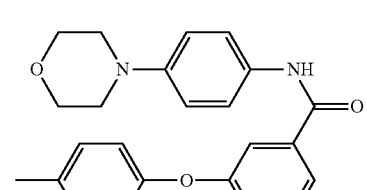 |
| 83 | 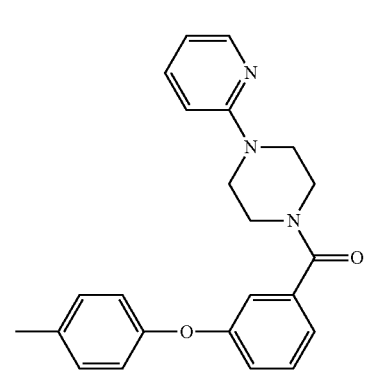 |
| 84 | 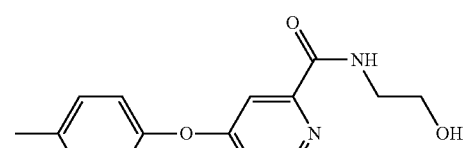 |
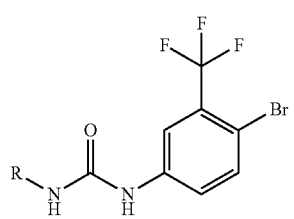
| Example entry | R |
|---|---|
| 85 | 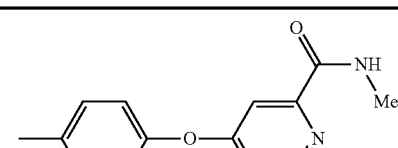 |
| 86 | 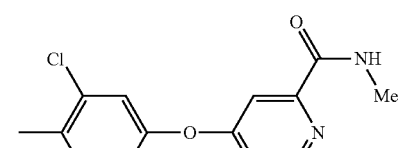 |
| 87 | 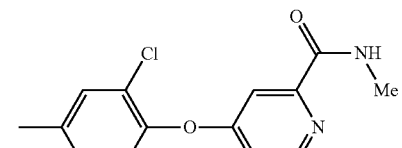 |
| 88 | 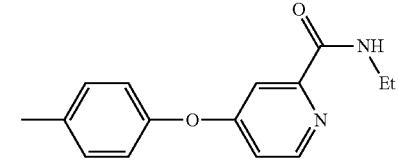 |
| 89 | 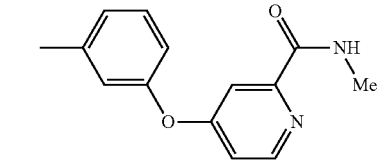 |
| 90 | 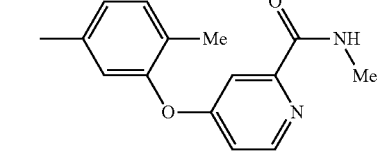 |
| 91 | 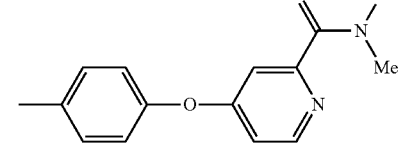 |
| 92 | 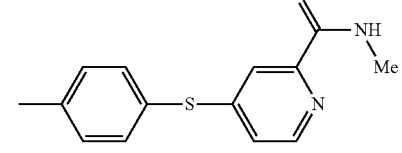 |
| 93 | 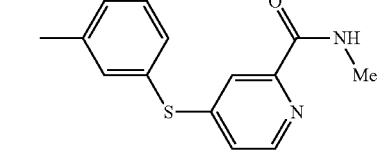 |

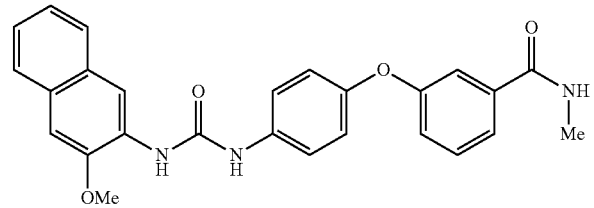 [SMILES: CNC(=O)c1cccc(Oc2ccc(NC(=O)Nc3cc4ccccc4cc3OC)cc2)c1]

| Example entry | Structure |
|---|---|
| 103 | 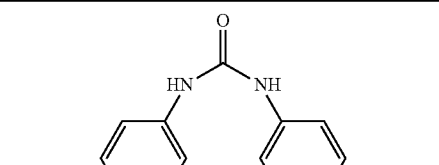 | or a physiologically acceptable salt, solvate, hydrate or stereoisomer thereof, said compounds are published as compounds of general formula (I) in International patent application PCT/US00/00648, published as WO 00/42012 A1 on Jul. 20, 2000, which is incorporated herein by reference in its entirety. In WO 00/42012 A1, said compounds of general formula (I) are described on pp. 2 et seq., they may be synthesized according to the methods given therein on pp. 14 et seq., and are exemplified as specific compound Example entries 1 to 41 and 43 to 103 on pp. 53 to 88, therein.

As mentioned supra, a further specific example of said compounds of general formula (I) of WO 00/42012 A1 is of structure (Ia), which is herein referred to as the "compound of formula (Ia)":

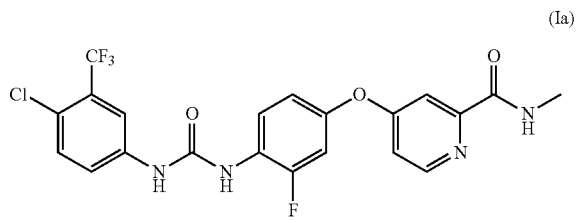
(Ia)

said compound of formula (Ia) is published as compound of formula (I) in International patent application PCT/US2004/023500, published as WO 2005/009961 A2 on Feb. 3, 2005, which is incorporated herein by reference in its entirety. Said compound of formula (Ia) may be synthesized as in WO 2005/009961 A2, according to the methods given therein on pp. 45 et seq. therein, and may be a free base (Example 1 of WO 2005/009961 A2), a hydrochloride salt (Example 2 of WO 2005/009961 A2), a mesylate salt (Example 3 of WO 2005/009961 A2) or a phenylsulfonate salt (Example 4 of WO 2005/009961 A2).

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with an embodiment of the above-mentioned aspects of the present invention, said combinations are of:

component B: which is one or more N-(2-arylamino)aryl sulfonamide compounds of general formula (II):

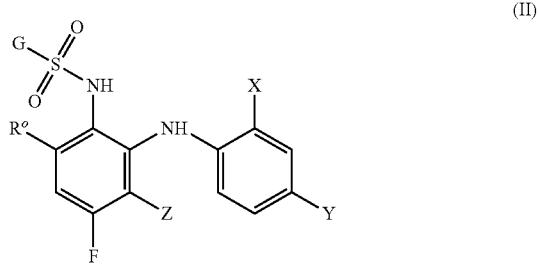
(II)

where G is $R_{1a}$, $R_{1b}$, $R_{1c}$, $R_{1d}$, $R_{1e}$, $Ar_1$, $Ar_2$ or $Ar_3$; $R^o$ is H, halogen, $C_1$-$C_6$ alkyl, $C_1$-$C_4$ alkoxy, $C_3$-$C_6$ cycloalkyl, $C_2$-$C_6$ alkenyl, $C_2$-$C_6$ alkynyl, said alkyl, cycloalkyl, alkenyl, and alkynyl groups optionally substituted with 1-3 substituents selected independently from halogen, OH, CN, cyanomethyl, nitro, phenyl, and trifluoromethyl, and said $C_1$-$C_6$ alkyl and $C_1$-$C_4$ alkoxy groups also optionally substituted with $OCH_3$ or $OCH_2CH_3$; X is F, Cl or methyl; Y is I, Br, $C_1$, $CF_3$, $C_1$-$C_3$ alkyl, $C_2$-$C_3$ alkenyl, $C_2$-$C_3$ alkynyl, cyclopropyl, phenyl, pyridyl, pyrazolyl, OMe, OEt, or SMe, where all said methyl, ethyl, $C_1$-$C_3$ alkyl, and cyclopropyl groups of X and Y are optionally substituted with OH, all said phenyl, pyridyl, pyrazolyl groups of Y are optionally substituted with halogen, acetyl, methyl, and trifluoromethyl, and all said methyl groups of X and Y are optionally substituted with one, two, or three F atoms; and Z is H or F, where $R_{1a}$ is methyl, optionally substituted with 1-3 fluorine atoms or 1-3 chlorine atoms, or with OH, cyclopropoxy, or $C_1$-$C_4$ alkoxy, where the $C_1$-$C_4$ alkyl moieties of said $C_1$-$C_4$ alkoxy groups are optionally substituted with one hydroxy or methoxy group, and where all $C_2$-$C_4$ alkyl groups within said $C_1$-$C_4$ alkoxy are optionally further substituted with a second OH group;

$R_{1b}$ is $CH(CH_3)$—$C_{1-3}$ alkyl or $C_3$-$C_6$ cycloalkyl, said methyl, alkyl, and cycloalkyl groups optionally substituted with 1-3 substituents selected independently from F, Cl, Br, I, OH, $C_1$-$C_4$ alkoxy, and CN;

$R_{1c}$ is $(CH_2)_nO_mR'$, where m is 0 or 1; where, when m is 1, n is 2 or 3, and when m is 0, n is 1 or 2; and where R' is $C_1$-$C_6$ alkyl, optionally substituted with 1-3 substituents selected independently from F, Cl, OH, OCH$_3$, OCH$_2$CH$_3$, and C$_3$-C$_6$ cycloalkyl;

R$_{1d}$ is C(A)(A')(B)— where B, A, and A' are, independently, H or C$_{1-4}$ alkyl, optionally substituted with one or two OH groups or halogen atoms, or A and A', together with the carbon atom to which they are attached, form a 3- to 6-member saturated ring, said ring optionally containing one or two heteroatoms selected, independently, from O, N, and S and optionally substituted with one or two groups selected independently from methyl, ethyl, and halo;

R$_{1e}$ is benzyl or 2-phenyl ethyl, in which the phenyl group is optionally substituted

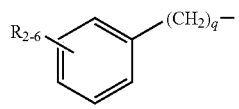

where q is 1 or 2, R$_2$, R$_3$ and R$_4$ are, independently, H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl, and R$_4$ may also be nitro, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazol-1H-tetrazolyl, N-morpholinyl carbonylamino, N-morpholinylsulfonyl, and N-pyrrolidinylcarbonylamino; R$_5$ and R$_6$ are, independently, H, F, Cl, or methyl;

Ar$_1$ is

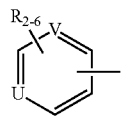

where U and V are, independently, N, CR$_2$ or CR$_3$; R$_2$, R$_3$ and R$_4$ are, independently, H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl, and R$_4$ may also be nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholinylcarbonylamino, N-morpholinylsulfonyl and N-pyrrolidinylcarbonylamino; R$_5$ and R$_6$ are, independently, H, F, Cl or methyl;

Ar$_2$ is

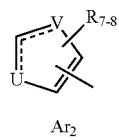

where the dashed line represents a double bond which may be located formally either between V and the carbon between U and V, or between U and the carbon between U and V; where U is —S—, —O— or —N═ and where, when U is —O— or —S—, V is —CH═, —CCl═ or —N═; and when U is —N═, V CH═, or —NCH$_3$—; R$_7$ and R$_8$ are, independently, H, methoxycarbonyl, methylcarbamoyl, acetamido, acetyl, methyl, ethyl, trifluoromethyl, or halogen.

Ar$_3$ is

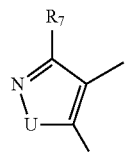

where U is —NH—, —NCH$_3$— or —O—; and R$_7$ and R$_8$ are, independently, H, F, Cl, or methyl;

or a physiologically acceptable salt, solvate, hydrate or stereoisomer thereof; said compounds are published as compounds of general formulae I, IA-1, IA-2, IB-1, IB-2, IC-1, IC-2, ID-1, ID-2, IE-1, IE-2, IIA-1, IIA-2, IIA-3, II-B, III-A, and III-B in International patent application PCT/US2006/028326, published as WO 2007/014011 A2 on Jul. 21, 2006, which is incorporated herein by reference in its entirety. In WO 2007/014011 A2, said compounds of general formulae I, IA-1, IA-2, IB-1, IB-2, IC-1, IC-2, ID-1, ID-2, IE-1, IE-2, IIA-1, IIA-2, IIA-3, II-B, III-A, and III-B are described on pp. 4 et seq., and pp. 19 et seq., they may be synthesized according to the methods given therein on pp. 39, et seq., and are exemplified as specific compound Examples 1 to 71 therein on pp. 41 to 103. Biological test data for certain of said compounds are given therein on pp. 104 to 111.

Said component B may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with another embodiment of the above-mentioned aspects of the present invention, said combinations are of:

component B: which is one or more N-(2-arylamino)aryl sulfonamide compounds of general formula (II), supra, which is selected from the list consisting of:

Example 1 N-(3,4-difluoro-2-(2-fluoro-4-iodophenylamino)phenyl)-methanesulfonamide:

Example 2 N-(3,4-difluoro-2-(2-fluoro-4-iodophenylamino)phenyl)cyclopropanesulfonmide:

Example 3: N-(3,4-difluoro-2-(2-fluoro-4-iodophenylamino)phenyl)propane-2-sulfonamide:

Example 4: N-(3,4-difluoro-2-(2-fluoro-4-iodophenylamino)phenyl)butane-1-sulfonamide:

Example 5: N-(3,4-difluoro-2-(2-fluoro-4-iodophenylamino)phenyl)-2,2,2-trifluoro ethane sulfonamide:

Example 6: N-(3,4-difluoro-2-(2-fluoro-4-iodophenylamino)phenyl)butane-2-sulfonamide:

Example 7: N-(3,4-difluoro-2-(2-fluoro-4-iodophenylamino)phenyl)-N-methyl cyclopropane sulfonamide:

Example 8: 1-Chloro-N-(3,4-difluoro-2-(2-fluoro-4-iodophenylamino)phenyl)methane sulfonamide:

Example 9: N-(3,4-difluoro-2-(2-fluoro-4-iodophenylamino)phenyl)-2-methylpropane-2-sulfonamide:

Example 10 N-(3,4-difluoro-2-(2-fluoro-4-iodophenylamino)phenyl)cyclopentanesulfonamide:

Example 11: N-(3,4-difluoro-2-(2-fluoro-4-iodophenylamino)phenyl)cyclohexanesulfonamide:

Example 12: N-(3,4-difluoro-2-(2-fluoro-4-iodophenylamino)phenyl)-1-methylcyclopropane-1-sulfonamide:

Example 13: N-(3,4-difluoro-2-(2-fluoro-4-iodophenylamino)phenyl)-1-(2,3-dihydroxypropyl)cyclopropane-1-sulfonamide:

Example 14: (S)—N-(3,4-difluoro-2-(2-fluoro-4-iodophenylamino)phenyl)-1-(2,3-dihydroxypropyl)cyclopropane-1-sulfonamide:

Example 15: (R)—N-(3,4-difluoro-2-(2-fluoro-4-iodophenylamino)phenyl)-1-(2,3-dihydroxypropyl)cyclopropane-1-sulfonamide:

Example 16: N-(3,4-difluoro-2-(2-fluoro-4-iodophenylamino)phenyl)-1-(2-hydroxyethyl)cyclopropane-1-sulfonamide:

Example 17: N-(3,4-difluoro-2-(2-fluoro-4-iodophenylamino)phenyl)-3-hydroxypropane-1-sulfonamide:

Example 18: N-(3,4-difluoro-2-(2-fluoro-4-iodophenylamino)phenyl)-2-methyl-5-(trifluoromethyl)furan-3-sulfonamide:

Example 19: N-(5-(N-(3,4-difluoro-2-(2-fluoro-4-iodophenylamino)phenyl)sulfamoyl)-methylthiazol-2-yl)acetamide:

Example 20: 5-(5-Chloro-1,2,4-thiadiazol-3-yl)-N-(3,4-difluoro-2-(2-fluoro-4-iodophenylamino)phenyl)thiophene-2-sulfonamide:

Example 21: N-(3,4-difluoro-2-(2-fluoro-4-iodophenylamino)phenyl)-3,5dimnethylisoxazole-4-sulfonamide:

Example 22: 5-Chloro-N-(3,4-difluoro-2-(2-fluoro-4-iodophenylamino)phenyl)-1,3-dimethyl-1H-pyrazole-4-sulfonamide:

Example 23: N-(3,4-difluoro-2-(2-fluoro-4-iodophenylamino)phenyl)-2,5-dimethylfuran-3-sulfonamide:

Example 24: N-(3,4-difluoro-2-(2-fluoro-4-iodophenylamino)phenyl)-1-methyl-3-(trifluoromethyl)-1H-pyrazole-4-sulfonamide:

Example 25: N-(3,4-difluoro-2-(2-fluoro-4-iodophenylamino)phenyl)-2,4-dimethylthiazole-5-sulfonamide:

Example 26: N-(3,4-difluoro-2-(2-fluoro-4-iodophenylamino)phenyl)-1,2-dimethyl-1H-imidazole-4-sulfonamide:

Example 27: N-(3,4-difluoro-2-(2-fluoro-4-iodophenylamino)phenyl)thiophene-3-sulfonamide:

Example 28: N-(3,4-difluoro-2-(2-fluoro-4-iodophenylamino)phenyl)furan-2-sulfonamide:

Example 29: N-(3,4-difluoro-2-(2-fluoro-4-iodophenylamino)phenyl)-5-methylthiophene-2-sulfonamide:

Example 30: 5-Chloro-N-(3,4-difluoro-2-(2-fluoro-4-iodophenylamino)phenyl)thiophene-2-sulfonamide:

Example 31: 5-Bromo-N-(3,4-difluoro-2-(2-fluoro-4-iodophenylamino)phenyl)thiophene-2-sulfonamide:

Example 32: 4-Bromo-N-(3,4-difluoro-2-(2-fluoro-4-iodophenylamino)phenyl)thiophene-3-sulfonamide:

Example 33: 4-Bromo-5-chloro-N-(3,4-difluoro-2-(2-fluoro-4-iodophenylamino)phenyl)thiophene-2-sulfonamide:

Example 34: 3-Bromo-5-chloro-N-(3,4-difluoro-2-(2-fluoro-4-iodophenylamino)phenyl)thiophene-2-sulfonamide:

Example 35: N-(3,4-difluoro-2-(2-fluoro-4-iodophenylamino)phenyl)-2,5-dimethylthiophene-3-sulfonamide:

Example 36: 2,5-Dichloro-N-(3,4-difluoro-2-(2-fluoro-4-iodophenylamino)phenyl)thiophene-3-sulfonamide:

Example 37: Methyl 3-(N-(3,4-difluoro-2-(2-fluoro-4-iodophenylamino)phenyl)sulfamoyl)thiophene-2-carboxylate:

Example 38: Methyl 5-(N-(3,4-difluoro-2-(2-fluoro-4-iodophenylamino)phenyl)sulfamoyl)-1-methyl-1H-pyrrole-2-carboxylate:

Example 39: N-(3,4-difluoro-2-(2-fluoro-4-iodophenylamino)phenyl)-5-methylisoxazole-4-sulfonamide:

Example 40: 3-Chloro-N-(3,4-difluoro-2-(2-fluoro-4-iodophenylamino)phenyl)propane-1-sulfonamide:

Example 41: N-(2-(4-chloro-2-fluorophenylamino)-3,4-difluorophenyl)cyclopropanesulfonamide:

Example 42: N-(3,4-difluoro-2-(4-iodo-2-methylphenylamino)phenyl)cyclopropanesulfonamide:

Example 43: N-(2-(4-tert-butyl-2-chlorophenylamino)-3,4-difluorophenyl)cyclopropanesulfonamide:

Example 44 N-(2-(2,4-dichlorophenylamino)-3,4-difluorophenyl)cyclopropanesulfonamide:

Example 45: 3-Chloro-N-(3,4-difluoro-2-(2-fluoro-4-trifluoromethyl)phenylamino)phenyl)propane-1-sulfonamide:

Example 46 N-(3,4-difluoro-2-(2-chloro-4-trifluoromethyl)phenylamino)methanesulfonamide:

Example 47: 3-Chloro-N-(3,4-difluoro-2-(2-chloro-4-trifluoromethyl)phenylamino)phenyl)propane-1-sulfonamide:

Example 48: 3-Chloro-N-(3,4-difluoro-2-(2-bromo-4-trifluoromethyl)phenylamino)phenyl)propane-1-sulfonamide:

Example 49: Cyclopropanesulfonic acid (3,4,6-trifluoro-2-(2-fluoro-4-iodo-phenylamino)-phenyl)-amide:

Example 50: N-(3,4-difluoro-2-(4-fluoro-2-iodophenylamino)-6-ethoxyphenyl)cyclopropane sulfonamide:

Example 51: Methylsulfonic acid (3,4-difluoro-2-(2-fluoro-4-iodo-phenylamino)-6-methoxy-phenyl)-amide:

Example 52: 1-(2,3-Dihydroxy-propyl)-cyclopropanesulfonic acid [3,4,6-trifluoro-2-(4-fluoro-2-iodo-phenylamino)-phenyl]-amide:

Example 53: (S)-1-(2,3-dihydroxypropyl)-N-(3,4,6-trifluoro-2-(2-fluoro-4-iodophenylamino)phenyl)cyclopropane-1-sulfonamide:

Example 54: (R)-1-(2,3-dihydroxypropyl)-N-(3,4,6-trifluoro-2-(2-fluoro-4-iodophenylamino)phenyl)cyclopropane-1-sulfonamide:

Example 55: N-(3,4-difluoro-2-(2-fluoro-4-iodophenylamino)phenyl)-1-(2,3-dihydroxypropyl)cyclopropane-1-sulfonamide:

Example 56: (S)—N-(3,4-difluoro-2-(2-fluoro-4-iodophenylamino)-6-methoxyphenyl)-1-(2,3-dihydroxypropyl)cyclopropane-1-sulfonamide:

Example 57: (R)—N-(3,4-difluoro-2-(2-fluoro-4-iodophenylamino)-6-methoxyphenyl)-1-(2,3-dihydroxypropyl)cyclopropane-1-sulfonamide:

Example 58: 1-(2-hydroxyethyl)-N-(3,4,6-trifluoro-2-(2-fluoro-4-iodophenylamino)phenyl)cyclopropane-1-sulfonamide:

Example 59: N-(3,4-difluoro-2-(2-fluoro-4-iodophenylamino)-6-methoxyphenyl)-1-(2-hydroxyethyl)cyclopropane-1-sulfonamide:

Example 60: N-(3,4-difluoro-2-(2-fluoro-4-iodophenylamino)-6-methoxyphenyl)-1-(3-hydroxy-2-(hydroxymethyl)propyl)cyclopropane-1-sulfonamide:

Example 61: N-(3,4-difluoro-2-(2-fluoro-4-iodophenylamino)-6-methoxyphenyl)cyclobutane sulfonamide:

Example 62: N-(3,4-difluoro-2-(2-fluoro-4-iodophenylamino)-6-methylphenyl)-1-(2,3-dihydroxypropyl)cyclopropane-1-sulfonamide:

Example 63: 1-(2,3-Dihydroxypropyl)-N-(6-ethyl-3,4-difluoro-2-(2-fluoro-4-iodophenylamino)phenyl)cyclopropane-1-sulfonamide:

Example 64: N-(3,4-difluoro-2-(2-fluoro-4-iodophenylamino)-6-(2-methoxyethoxy)phenyl)-1-(2,3-dihydroxypropyl)cyclopropane-1-sulfonamide:

Example 65: 2,4-dichloro-N-(3,4-difluoro-2-(2-fluoro-4-iodophenylamino)phenyl)benzene sulfonamide:
Example 66: 2-chloro-N-(3,4-difluoro-2-(2-fluoro-4-iodophenylamino)phenyl)-4-(trifluoromethyl)benzenesulfonamide:
Example 67: N-(3,4-difluoro-2-(2-fluoro-4-iodophenylamino)phenyl)-2-(trifluoromethoxy)benzene sulfonamide:
Example 68: 4-(N-(3,4-difluoro-2-(2-fluoro-4-iodophenylamino)phenyl)sulfamoyl)benzoic acid:
Example 69: N-(3,4-difluoro-2-(2-fluoro-4-iodophenylamino)phenyl)benzenesulfonamide:
Example 70: N-(3,4-difluoro-2-(2-fluoro-4-iodophenylamino)phenyl)-2-fluorobenzene sulfonamide:
Example 71: N-(3,4-difluoro-2-(2-fluoro-4-methylphenylamino)phenyl)cyclopropanesulfonamide;
or a physiologically acceptable salt, solvate, hydrate or stereoisomer thereof.

Said component B may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with an embodiment, the present invention relates to a combination of any component A mentioned herein with any component B mentioned herein, optionally with any component C mentioned herein.

In a particular embodiment, the present invention relates to a combination of a component A with a component B, optionally with a component C, as mentioned in the Examples section herein.

Useful Forms of Components A and B of the Combinations of the Present Invention

As mentioned supra, either or both of components A and B of any of the combinations of the present invention may be in a useful form, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Pharmaceutical Formulations of Components A and B of the Combinations of the Present Invention As mentioned supra, the components A or B may, independently from one another, be in the form of a pharmaceutical formulation which is ready for use to be administered simultaneously, concurrently, separately or sequentially. The components may be administered independnently of one another by the oral, intravenous, topical, local installations, intraperitoneal or nasal route.

Said compositions can be utilized to achieve the desired pharmacological effect by administration to a patient in need thereof. A patient, for the purpose of this invention, is a mammal, including a human, in need of treatment for the particular condition or disease. Therefore, the present invention includes combinations in which components A and B, independently of one another, are pharmaceutical formulations compositions that are comprised of a pharmaceutically acceptable carrier and a pharmaceutically effective amount of a said component. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of component, and/or combination. A pharmaceutically effective amount of a combination is preferably that amount which produces a result or exerts an influence on the particular condition being treated. The combinations of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the combinations can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the combinations of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The combinations of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized Powder for IV Administration:

A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Cancer

Within the context of the present invention, the term "cancer" includes, but is not limited to, cancers of the breast, lung, brain, reproductive organs, digestive tract, urinary tract, liver, eye, skin, head and neck, thyroid, parathyroid and their distant metastases. Those disorders also include multiple myeloma, lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The present invention relates to a method for using the combinations of the present invention, to treat cancer, as described infra, particularly mammalian NSCLC, CRC, melanoma, pancreatic cancer, hepatocyte or breast cancer. Combinations can be utilized to inhibit, block, reduce, decrease, etc., cell proliferation and/or cell division, and/or produce apoptosis, in the treatment or prophylaxis of cancer, in particular NSCLC, CRC, melanoma, pancreatic cancer, hepatocyte carcinoma or breast cancer. This method comprises administering to a mammal in need thereof, including a human, an amount of a combination of this invention, or a pharmaceutically acceptable salt, isomer, polymorph, metabolite, hydrate, solvate or ester thereof; etc. which is effective for the treatment or prophylaxis of cancer, in particular NSCLC, CRC, melanoma, pancreatic cancer, hepatocyte carcinoma or breast cancer.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment or prophylaxis of cancer, in particular NSCLC, CRC, melanoma, pancreatic cancer, hepatocyte carcinoma or breast cancer, by standard toxicity tests and by standard pharmacological assays for the determination of treatment of the conditions identified above in mammals, and by comparison of these results with the results of known medicaments that are used to treat these conditions, the effective dosage of the combinations of this invention can readily be determined for treatment of the indication. The amount of the active ingredient to be administered in the treatment of the condition can vary widely according to such considerations as the particular combination and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1,500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific combination employed, the age and general condition of the patient, time of administration, route of administration, rate of excretion of the drug, drug combinations, and the like. The desired mode of treatment and number of doses of a combination of the present invention or a pharmaceutically acceptable salt or ester or composition thereof can be ascertained by those skilled in the art using conventional treatment tests.

Therapies Using Combinations of Component A as Described Supra, Component B as Described Supra, and Component C: One or More Further Pharmaceutical Agents.

The combinations of component A and component B of this invention can be administered as the sole pharmaceutical agent or in combination with one or more further pharmaceutical agents where the resulting combination of components A, B and C causes no unacceptable adverse effects. For example, is the combinations of components A and B of this invention can be combined with component C, i.e. one or more further pharmaceutical agents, such as known anti-angiogenesis, anti-hyper-proliferative, antiinflammatory, analgesic, immunoregulatory, diuretic, antiarrhytmic, anti-hypercholesterolemia, anti-dyslipidemia, anti-diabetic or anti-viral agents, and the like, as well as with admixtures and combinations thereof.

Component C, can be one or more pharmaceutical agents such as aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexamethasone, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthrohydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, lenalidomide, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel (when component B is not itself paclitaxel), pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solumedrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thalidomide, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Alternatively, said component C can be one or more further pharmaceutical agents selected from gemcitabine, paclitaxel (when component B is not itself paclitaxel), cisplatin, carboplatin, sodium butyrate, 5-FU, doxirubicin, tamoxifen, etoposide, trastumazab, gefitinib, intronA, rapamycin, 17-AAG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Optional anti-hyper-proliferative agents which can be added as component C to the combination of components A and B of the present invention include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use as component C with the combination of components A and B of the present invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel (when component B is not itself paclitaxel), pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use as component C with the combination of components A and B of the present invention include but are not limited to other anti-cancer agents such as epothilone and its derivatives, irinotecan, raloxifen and topotecan.

Generally, the use of cytotoxic and/or cytostatic agents as component C in combination with a combination of components A and B of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

EXAMPLES

Abbreviations used in the present Examples section are:
"cA" means the compound of formula (Ia):

(Ia)

which is compound of formula (I) in International patent application PCT/US2004/023500, published as WO 2005/009961 A2 on Feb. 3, 2005, (which is incorporated herein by reference in its entirety), and is which is an example of component A as described and defined herein.

"cB" means compound Example 56 of WO 2007/014011 A2, i.e. (S)—N-(3,4-difluoro-2-(2-fluoro-4-iodophenylamino)-6-methoxyphenyl)-1-(2,3-dihydroxypropyl)cyclopropane-1-sulfonamide, of structure:

which is an example of component B as described and defined herein.

The invention is demonstrated in the following Example which is not meant to limit the invention in any way:

Example

Method: In Vitro Combination Studies

The combination effects of cA and cB were evaluated using combination index isobologram analysis. The efficacy parameters were the median effect in a 72-hour cell proliferation assay. Briefly, cells were plated in 384-well plate with 25 μl medium. After 24 hours, 5 μL of experimental media containing either cB, cA, or the combination of cB plus cA at different ratio (0.9xcB+0.1xcA, 0.7xcB+0.3xcA, 0.5xcB+0.5xcA, 0.3xcB+0.7xcA, 0.1xcB+0.9xcA) were used to make serial three-fold dilutions to generate 7 doses curves. Experiments were conducted in triplicates.

The mapping $EC_{50}/IC_{50}$ were were determined by means of a 4-parameter fit using the company's own software. The corresponding component doses of cB and cA at the $E(I)C_{50}$ were calculated and used for plotting isobolograms. Multiple drug effect was analyzed as described by Chou (Pharmacology Reviews 2006) and the combination index was calculated using the formula:

Combination Index=$[cBx]/cB'+[cAx]/cA'$ cBx and cAx refer to the cB and cA concentration at $EC_{50}/IC_{50}$ in combination cB' and cA' refer to the $EC_{50}/IC_{50}$ values of cB and cA, respectively, as a single agent. In this analysis, combination index 0-0.3, 0.3-0.6, and 0.6-0.9, were defined as very strong synergy, strong synergy and synergy, respectively.

Results:

In vitro combination studies between cB and cA were performed in the two HCC cell lines PLC/PRF/5 and Hep3B. In the Hep3B cell line combination index values between 0.71-0.33 were measured in 4 out of 5 dose combination ratios, indicating synergistic or even strong synergistic effects for the combination of the two drugs.

In the PLC/PRF/5 cell line combination index values between 0.63-0.83 in 5 out of 5 different combination ratios were measured, indicating a synergistic effect for the combination of cB and cA.

See FIG. 1/2

Figure 2:
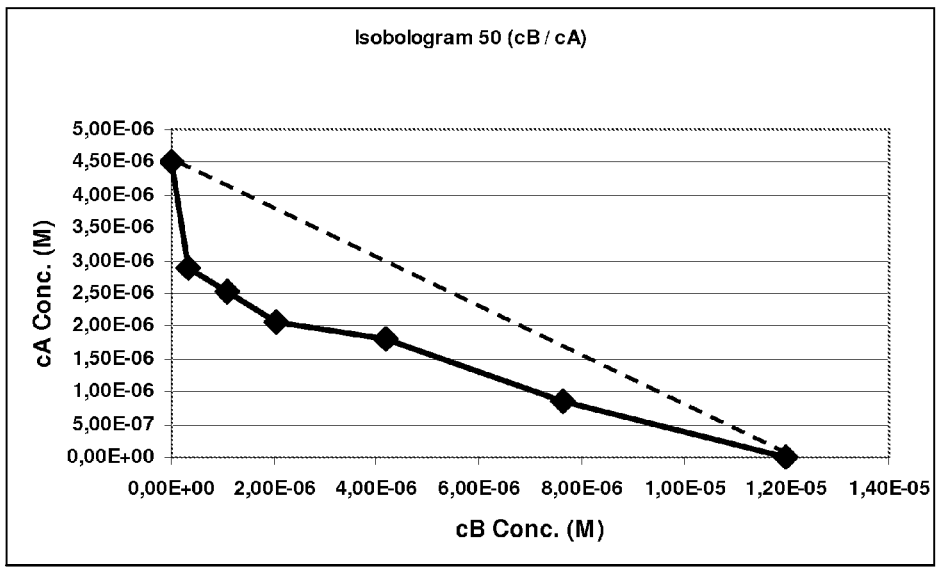

FIG. 1/2:

Shows an isobologram and combination index analysis on the drug-drug interaction between cB and cA against proliferation in HCC cancer cell is line Hep3B. Experiments were conducted as described in the method. The top concentrations of cB and cA are 30 μM. MAPPING $IC_{50}$ refers to the $IC_{50}$ obtained from the dose-response curve of either cB or cA alone, or cB plus cA with the ratio indicated in the table, where the top relative concentration is defined as See FIG. 2/2

FIG. 2/2:

Shows an isobologram and combination index analysis on the drug-drug interaction between cB and cA against proliferation in HCC cancer cell line PLC/PRF/5. Experiments were conducted as described in the method. The top concentrations of cB and cA are 30 μM. MAPPING $IC_{50}$ refers to the $IC_{50}$ obtained from the dose-response curve of either cB or cA alone, or cB plus cA with the ratio indicated in the table, where the top relative concentration is defined as 1.

The combination with omega-carboxyaryl-substituted diphenyl urea compounds can also include more than one compound: it could be two, or more compounds.

The invention claimed is:

1. A combination comprising component A:

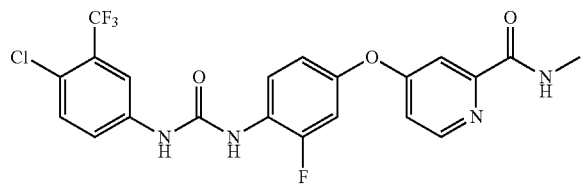 [SMILES: CNC(=O)c1cc(Oc2ccc(NC(=O)Nc3ccc(Cl)c(C(F)(F)F)c3)c(F)c2)ccn1]

or a physiologically acceptable salt, solvate, hydrate or stereoisomer thereof; and
component B:
(S)—N-(3,4-difluoro-2-(2-fluoro-4-iodophenylamino)-6-methoxyphenyl)-1-(2,3-dihydroxypropyl)cyclopropane-1-sulfonamide
or a physiologically acceptable salt, solvate, hydrate or stereoisomer thereof.

2. A method for preparing a medicament for treating of hepatocyte carcinoma comprising including a combination according to claim 1 in said medicament.

3. A method for treating hepatocyte carcinoma in a subject, comprising administering to said subject a therapeutically effective amount of the combination according to claim 1.

4. A kit comprising a combination of:
component A:

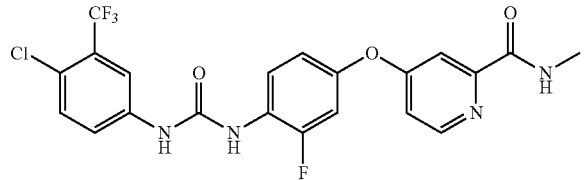 [SMILES: CNC(=O)c1cc(Oc2ccc(NC(=O)Nc3ccc(Cl)c(C(F)(F)F)c3)c(F)c2)ccn1]

or a physiologically acceptable salt, solvate, hydrate or stereoisomer thereof; and
component B:
(S)—N-(3,4-difluoro-2-(2-fluoro-4-iodophenylamino)-6-methoxyphenyl)-1-(2,3-dihydroxypropyl)cyclopropane-1-sulfonamide
or a physiologically acceptable salt, solvate, hydrate or stereoisomer thereof.

5. The kit according to claim 4, wherein said component A is:

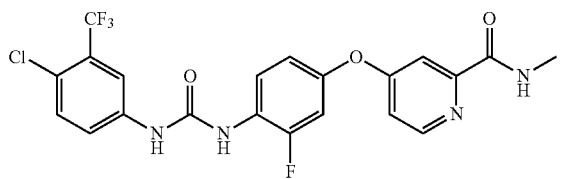 [SMILES: CNC(=O)c1cc(Oc2ccc(NC(=O)Nc3ccc(Cl)c(C(F)(F)F)c3)c(F)c2)ccn1]

and
component B is:
(S)—N-(3,4-difluoro-2-(2-fluoro-4-iodophenylamino)-6-methoxyphenyl)-1-(2,3-dihydroxypropyl)cyclopropane-1-sulfonamide.

6. The combination to claim 1, wherein said component A is:

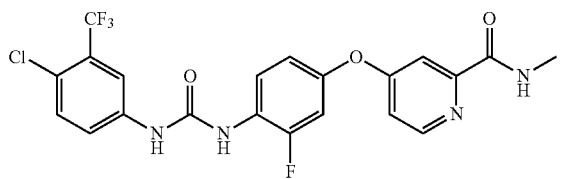 [SMILES: CNC(=O)c1cc(Oc2ccc(NC(=O)Nc3ccc(Cl)c(C(F)(F)F)c3)c(F)c2)ccn1]

and
component B is:
(S)—N-(3,4-difluoro-2-(2-fluoro-4-iodophenylamino)-6-methoxyphenyl)-1-(2,3-dihydroxypropyl)cyclopropane-1-sulfonamide.

7. The combination of claim 1, in which both or either of said components A and B are in the form of a pharmaceutical formulation which is ready for use to be administered simultaneously, concurrently, separately or sequentially.

8. The combination of claim 1, further comprising component C: one or more further pharmaceutical agents.

9. The kit of claim 4, in which both or either of said components A and B are in the form of a pharmaceutical formulation which is ready for use to be administered simultaneously, concurrently, separately or sequentially.

10. The kit of claim 4, further comprising component C: one or more further pharmaceutical agents.

* * * * *